"(12) United States Patent
Simons et al.

(10) Patent No.: US 8,095,381 B2
(45) Date of Patent: Jan. 10, 2012

(54) REMOTE PATIENT SUPPORT AND CARE BY RELATIVES

(75) Inventors: David P. L. Simons, Eindhoven (NL); Eugene Ivanov, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 393 days.

(21) Appl. No.: 11/721,179

(22) PCT Filed: Dec. 9, 2005

(86) PCT No.: PCT/IB2005/054165
§ 371 (c)(1),
(2), (4) Date: Jun. 8, 2007

(87) PCT Pub. No.: WO2006/067662
PCT Pub. Date: Jun. 29, 2006

(65) Prior Publication Data
US 2009/0240521 A1  Sep. 24, 2009

Related U.S. Application Data

(60) Provisional application No. 60/637,809, filed on Dec. 21, 2004.

(51) Int. Cl.
*G06Q 50/00* (2006.01)
(52) U.S. Cl. ..................... 705/2; 705/3; 705/4; 600/300
(58) Field of Classification Search ....... 707/1, 999.108; 705/2–4; 600/300
See application file for complete search history.

(56) References Cited

U.S. PATENT DOCUMENTS

| 6,579,242 | B2 | 6/2003 | Bui et al. | |
| 2001/0039503 | A1* | 11/2001 | Chan et al. | 705/2 |
| 2002/0007286 | A1 | 1/2002 | Okamoto | |
| 2003/0036683 | A1 | 2/2003 | Kehr et al. | |
| 2003/0120516 | A1* | 6/2003 | Perednia | 705/3 |
| 2004/0006488 | A1* | 1/2004 | Fitall et al. | 705/2 |
| 2004/0054263 | A1 | 3/2004 | Moerman et al. | |
| 2004/0102683 | A1* | 5/2004 | Khanuja et al. | 600/300 |
| 2004/0130446 | A1 | 7/2004 | Chen et al. | |

FOREIGN PATENT DOCUMENTS

| JP | 2002092173 A | 3/2002 |
| WO | 0227999 A2 | 4/2002 |
| WO | 02058307 A2 | 7/2002 |

* cited by examiner

*Primary Examiner* — Gerald J. O'Connor
*Assistant Examiner* — Michelle Le

(57) ABSTRACT

A telemonitoring central server 12 supports secure data exchange between a number of users, such as a patient, family and friends, medical personnel, suppliers, and the like. A user authenticator 20 authenticates and authorizes a user to the system. Access control is driven by a number of static or dynamic access profiles that are assigned to each user. These profiles dictate the data to which the user is allowed access, the computations available to the user, and the manner in which data is displayed to the user. The presentation style is based on access role, user, age, background, result of previous interactions, information content, authentication level, and the like. Third-party services such as advertisements and discounts for "get well soon" items can also be provided to the user.

16 Claims, 1 Drawing Sheet

REMOTE PATIENT SUPPORT AND CARE BY RELATIVES

CROSS REFERENCE TO RELATED APPLICATIONS

Figure 1:
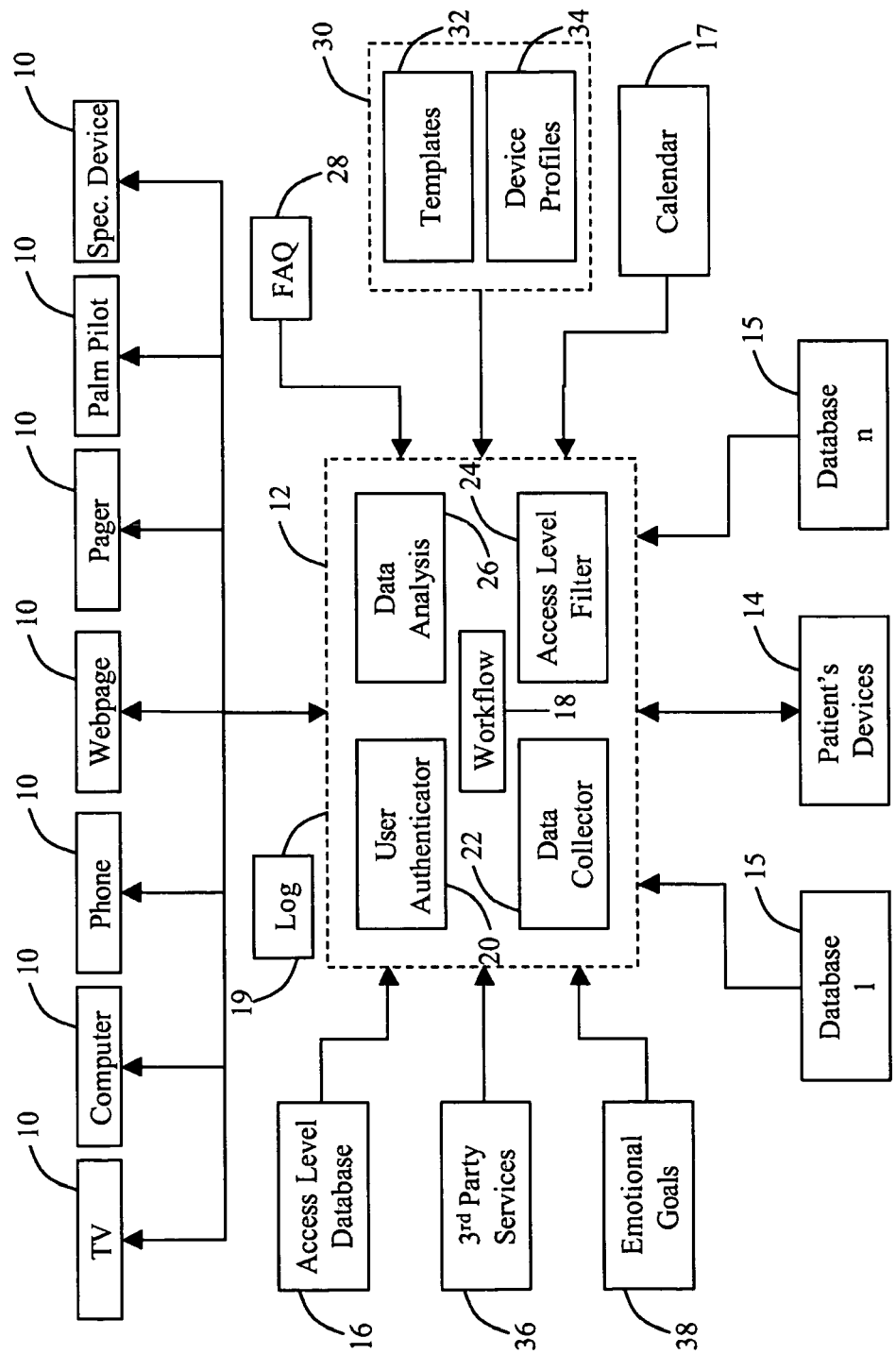

This application claims the benefit of U.S. provisional application Ser. No. 60/637,809 filed Dec. 21, 2004, which is incorporated herein by reference.

The present invention relates to the care of patients with long-term or chronic illnesses. More specifically, it relates to an information network that allows family, friends, and other caregivers of patients to remain better appraised of the patient's current medical conditions.

When a person is struck ill and requires extended term care as a patient, there are usually many family members and friends who have a very real and sincere interest in knowing how the patient's care is progressing and how the patient is doing. Typically, news of the patient's condition and how treatment and/or recovery etc. is going is passed along by word of mouth, telephone, e-mail, letter, and the like from those closest to the patient to others.

One drawback to this information relay is the "tall tale" tendency of stories to become distorted with each iteration or telling. Details of the patient's actual condition can become lost or distorted, and family members and friends may take action based on faulty information, or worry needlessly based on faulty information.

Depending on the patient's illness or condition, it may not be necessary for anyone to have actual contact with the patient for several hours or even days. Another disadvantage is that the latest information about the patient's condition may be old or obsolete.

Human interaction is sometimes difficult. Often medical conditions and illnesses can be quite complex and difficult to talk about between laypersons, both because of the complex nature of the subject matter, and some topics may be considered socially taboo. Moreover, it can become bothersome to the patient to have to answer the same questions time and time again, even though the person asking the question does not intend to be bothersome. Often it is easier for some people to absorb information at their own pace, rather than trying to absorb every detail as a person is relaying information by word of mouth.

The present application contemplates a new and improved patient information network which overcomes the above-referenced problems and others.

In accordance with one aspect of the present invention, a patient support network is provided. A patient data generating source generates on-line information about a patient, as well does at least one other source of information about the patient. A central server coordinates the patient data. At least one physician access device allows a physician of the patient to access information about the patient. At least one family member/friend access device remote from the patient allows at least one of a family member and a friend of the patient to access information about the patient via the central server.

In accordance with another aspect of the present invention, a method of patient care is provided. On-line information about a patient is generated and stored. Additional information about the patient is stored in at least one other location. The patient data is coordinated with a central server. Physician-appropriate information about the patient is provided to a physician of the patient. Family member/friend-appropriate information is provided to at least one of a friend and a family member through at least one family member/friend access device remote from the patient.

One advantage of the present invention resides in improved quality and accuracy of information relayed to family members and friends.

Another advantage resides in more current information available for family and friends.

Another advantage resides in improved access to a patient's physician.

Another advantage resides in the patient's control over dissemination of his or her information.

Another advantage resides in improved emotional support for the patient.

Another advantage resides in improved logistical support for the patient.

Another advantage resides in improved communication among family and friends of the patient.

Another advantage resides in user tailored information portrayal.

Another advantage resides in a user's control over access to information about the patient.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

FIG. 1 is a diagrammatic illustration of a preferred embodiment of a patient information network.

With reference to FIG. 1, a preferred embodiment of the patient support network is shown. A user, via an access device 10, accesses information about a patient. The access device 10 also allows the user to pose questions, send messages to the patient, order gifts for the patient, etc. The access device 10 can come in a variety of different forms, depending on the technical savvy of the user. Some of the contemplated devices are a dedicated interactive television channel, computer software, a telephone, a webpage accessible from any computer with internet access, a pager, a palm pilot or handheld PC, electronic information kiosks, or a device dedicated to this one purpose. Certainly other devices could perform the required tasks of the access device, and the examples above are not intended to be an exhaustive list, only some possible options. Possible users include the patient, family and friends of the patient, the patient's physician(s), other medical staff caring for the patient, and medical suppliers. Again, this is only a list of possible users, other users are certainly contemplated.

The access devices 10 communicate with a central server 12, which compiles information about the patient. The information about the patient comes from multiple sources. First, information is gathered from the patient's personal monitoring equipment 14. This includes any equipment that is directly monitoring the patient's condition, such as pulse oximetry meters, pulse rate monitors, blood pressure monitors, intravenous pumps, thermometers, etc. The patient also provides data through a personal input device to provide information such as "I'm doing fine" and the like. Additionally, information about the patient comes from additional ancillary sources 15. These sources at least include a hospital database that keeps a record of dates and times of admitting, scheduled procedures, performed procedures, etc., and doctor's notes e.g., the patient's "chart." Information about the patient also comes from other sources, such as preferred medical providers, (a history of orders, etc.) the patient's primary care physician, (medical history etc.) general informational and educational materials about the patient's condition, plus myriad other sources. The additional sources also include laboratory results and physician's records that are not part of the hospital database. While the present application certainly has exemplary utility in communicating with friends, family, and other persons who are remote from the patient, it is also contemplated that a user be residing with the patient, (i.e. in the same home) and still be able to access information about the patient via the central server 12.

To describe the central server 12 further, it performs a number of ad-hoc interactions between the system users, such as a video or telephone conference between a number of system users (e.g. patient with family and doctor) or family and friends sending a message to a medical professional with a question about the patient. Specifically, the central server 12 includes a video/audio conferencing subsystem which connects with an access device interface 10 to facilitate conference telephone calls, video phone picture exchanges, video internet conferences, internet text messaging, and the like. The central server 12 also includes a logistics support system to support interactions between system users by a request from other system components, such as different reminders and alerts about logistics operations (refills, doctor's visits, delivery statuses, etc.) from a calendar system 17. The server 12 has a simple built-in workflow engine 18 or can interface with an already-existing engine through open interfaces (e.g. HL7, SAP, or other interfaces known in the art). The workflow engine 18 preferably handles the managing of processes, the sharing of information, and the administration of the central server 12. Preferably, the server contains a log 19 for recording the system's processes for access audition, accountability, or other purposes.

The patient has the option of selecting a level of access for of the above-listed parties to the information available about the patient. To this end, each user is assigned a user profile. First, these user profiles identify the particular user as being associated with a certain patient. If the user is associated with multiple patients, the user may be prompted as to about patient about whom they are presently inquiring. Additionally, the user profiles also include access levels. These access levels are stored in an access level database 16. The access levels can be as simple as low medium and high access, where low access users have access to only the most superficial of information, such as dates of hospital stays and visiting hours, while high access users have access to all of the information. These levels can also be tailored to the individual user by the patient or physician, possibly allowing higher levels of access to close family members and friends, while allowing lower access to more distant relatives and casual acquaintances. For instance, a patient may want to allow all users to have access to general materials about his condition, but limit access to his vital sign readings to himself and his physician. Moreover, the patient himself may have limited access, say, being restricted from doctor's notes, as he may read something disturbing and be unnecessarily worried without proper explanation.

When a user logs on to the central server 12, they go through a user authentication process arbitrated by a user authenticator 20. The authenticator 20 is integrated into the central server 12 but is shown as a separate entity in FIG. 1 for ease of understanding. Authentication preferably is provided in the form of a username and credentials, so that the user can access the patient information from any available terminal (such as a webpage or information kiosk in a hospital). The credentials can come in the form of a password, biometrics (fingerprints, voice/face recognition and the like) RF ID, etc. Authentication is optionally linked with a certain device, as in the case with a dedicated TV channel, computer cookie, cellular phone, pager, palm pilot, or dedicated interface. In these cases, the user does not have to provide credentials, but rather an originating instrument identifier, such as a telephone number.

Once the user is identified and authenticated, a data collector 22 sets about gathering data from the sources 14, 15. The data can be pre-gathered in advance for optimization reasons. For instance, information from the source 14 may be pre-gathered periodically, the user having access to the latest gathered data. What data is collected is limited by an access level filter 24 that takes the authenticated access level of the user and filters out the data that is restricted to the particular user. The collected data, or reference thereto, is stored and analyzed by a data analyzer 26. The data analyzer 26 applies event recognition patterns and rules, optionally triggering a system event. At this point, optionally a human, such as a medical professional, is involved in the loop. For instance if the user has posed a question, the data analyzer 26 uses business logic, for example, to analyze the question and decide whether to refer the user to a list of frequently asked questions 28, if it determines that the answer is likely to be there, or to contact a medical professional, (via e-mail or the like) or to assist the user in making the question more specific. Once again, the data collector 22 and access level filter 24 are preferably integral portions of the central server 12 but shown as separate entities for simplicity of understanding.

After the data to which the user has access is collected and processed, it is presented to the user. The central server 12 determines how to present the information to the user based on the user's profile. In addition to identifying the user's association and access level, the user profile also identifies the access device that the user is using, and display preferences, where applicable. Preferably, the user retains control over access to information about the patient for as long as the user wants or is allowed by his access level. For instance, the user can view the information once per day, once every couple of weeks, once every month, etc. The user can receive e-mail remainders, utilize SMS web access etc. Naturally, these are but illustrative examples available to the user, many more access methods are contemplated. The display format is dependant on the device that the user is using, medical savvy of the user, age of the user, (e.g. child, teenager, adult) background, result of previous interactions, information content (acuity, amount, difficulty level) access level, and other factors. For instance, a patient may have a friend user who is a doctor, and the information presented to that friend may be quite technical; whereas, the same information presented to a layperson friend may be relatively simple, that is, less technical, but easier to understand. The central server 12 accesses a presentation database 30 that contains presentation templates 32 and device profiles 34. Based on the user's profile, the central server 12 selects a presentation that corresponds to the identified user. Data is then presented to the user based on the selected presentation profile.

In the preferred embodiment, the patient's instruments 14 and user interface are continuously monitored. As a result of data analysis, the system triggers an internal event, which leads to a communication with one or more system users. Where appropriate, the system contacts the patient's caregivers or $3^{rd}$ parties, such as medical supply outfits or pharmacies. The central server can access such parties through a $3^{rd}$ party services database 36. In one illustrative example, a patient's user interface reminds the patient to take a prescribed medication at the prescribed times throughout the day. The central server 12 keeps a tally of how much of that medication the patient should have taken. When the central server 12 detects that the patient is running low on that medication, it submits an order to a pharmacy for a refill. Similarly, with elective medications, such as pain killers, the central server 12 queries the patient periodically to see if the patient's supply is running low. If the patient responds affirmatively, the server 12 puts in an order to the pharmacy to refill that prescription, if it is within the doctor's orders.

Also available to the user are a number of third party services. An advertisement database 36 contains services and products that are available to the user. For example, when the central server 12 presents the user with information about the patient, it may also consult the advertisement database to provide the user with ads or discounts for products (flowers, balloons, etc.) that the user may want to purchase for the patient. As another example, where the user is responsible for prescriptions or medical supplies the database 36 provides advertisements and coupons relating to the prescriptions or supplies. The central server 12 selects the type of ads and services to present to the user based on the profile of the patient, and on the profile of the user. Similarly for the emotional well-being of the patient, an emotional goals database 38 is accessible by users. Communications from family and friends to the patient often have additional supportive or emotional roles. To aid the user in portraying support and positive feelings to the patient, the emotional goals database contains a number of emotional artifacts, such as icons, music, videos, parts of text, conversation templates, and the like. The user can include these along with the communication to the patient to help keep the patient in high spirits.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

The invention claimed is:

1. A patient care network comprising:
   a patient data generating source that generates on-line medical information about a patient;
   a central server for coordinating patient data;
   at least one family member/friend access device by which at least one of a family member user and a friend user of the patient accesses the medical information about the patient via the central server;
   a patient device by which the patient accesses the medical information;
   a user authentication device that:
      authenticates a family member or friend user as an authorized user before granting access to the medical information to the family member or friend user,
      after authorizing a family member or friend user, determines one of a plurality of authorization levels, the determined level dictates to which medical information the family member or friend user is granted access, the authorization level for each authorized family member or friend user being set by the patient, the plurality of authorization levels including at least three different authorization levels, and
      determines a presentation profile that describes a family member or friend user selected format for displaying the medical information to which the authorized family member or friend user has access,
   wherein the central server communicates the medical information to which the authorized family member or friend user is granted access to one of the family member/friend access devices for display in the authorized family member or friend user selected format.

2. The patient care network as set forth in claim 1, wherein the central server includes:
   a data collector that retrieves the medical information from the patient data generating source and at least one other source at the request of an authorized family member or friend user accessing the central server via the at least one family member/friend access device, and
   an access level filter that filters the retrieved medical information to limit access to a portion of the retrieved medical information depending upon the authorization level which the patient set for the authorized family member or friend user.

3. The patient care network as set forth in claim 1, further including:
   a communications network through family member or friend users communicate with each other and the patient.

4. The patient care network as set forth in claim 3, wherein the communications network provides communication with a physician communication device.

5. The patient care network as set forth in claim 3, further including:
   an emotional goals database by which the family members and friends transmit emotionally uplifting messages to the patient.

6. The patient care network as set forth in claim 1, further including:
   a database which stores general informal and educational materials;
   wherein the hospital database stores at least admitting information, scheduled procedures, and performed procedures; and
   wherein the central server communicates the admitting information, the scheduled procedures, the performed procedures, and the general and educational materials about a condition of the patient to an authorized family member or friend user at one of the authorization levels.

7. A method of patient care comprising:
   generating and storing on-line data about a patient;
   coordinating the patient data with a central server;
   determining capabilities of a family member/friend access device corresponding to each of the family member/friend users;
   storing a patient granted authorization level for each family member/friend user, there being at least three authorization levels, each authorization level granting access to different amounts of the patient data;
   authenticating each family member/friend user and each family member/friend access device before granting access to the patient information to the family member/friend user;
   retrieving the authorization level for each authenticated family member/friend user;
   retrieving information about the patient at the request of each authenticated family member/friend user accessing the central server via the at least one family member/friend access device;
   limiting the access to the retrieved information by each authenticated family member/friend user in accordance with the authorization level granted to each family member/friend user by the patient; and
   presenting the retrieved information limited in accordance with the authorization level of each family member/friend user appropriate patient on each family member/friend access device in a format that is appropriate for the determined capabilities of each family member/friend access device.

8. The method as set forth in claim 7, further including:
conferencing among the patient, the patient's physician, family members, and friends via a communications network and the central data server.

9. The method as set forth in claim 7, further including:
from at least one of the family member/friend access devices, accessing an emotional goals database associated with the central server to tailor emotionally supporting messages, the emotional goals database storing emotional goals for the patient; and sending the emotionally supporting messages to the central server to be posted for access by other family member/friends access devices and by a patient access device.

10. The method as set forth in claim 7, further including with the central server;
sending reminders to the patient to take medications;
tallying consumption of the medications;
determining when one or more of the medications are running low; and
when one or more of the medications is running low, sending a message to:
a pharmacy to refill a prescription for the medication.

11. The method as set forth in claim 7, further including with the central server;
sending reminders to the patient to take prescriptions or medical supplies;
tallying consumption of the prescriptions or medical supplies;
determining when one or more of the prescriptions or medical supplies are running low; and
when one or more of the prescriptions or medical supplies is running low:
providing advertisements and coupons relating to the prescriptions or medical supplies to a one of the family members/friends who is designated to obtain prescriptions or medical supplies.

12. The method as set forth in claim 7, further including:
generating a user profile for each family member/friend user, the user profile including the level of maturity of the user, the level of medical knowledge of the user, one of at least three authorization levels indicative of a level of patient data that the user is authorized to receive; and
filtering the stored patient data based on the user profile for each family member/friend user who requests patient data such that the requesting family member/friend user is provided with patient data limited in accordance with the requesting user's user profile.

13. A patient care network comprising:
patient monitoring equipment;
a central server that gathers medical information from the patient monitoring equipment and from a hospital database that keeps records of scheduled procedures, performed procedures, doctor's notes, patient's chart, and laboratory results;
a plurality of family/friend access devices by which users access the central server;
a patient access device by which the patient access the central server;
the central server further including:
a logistics support subsystem that issues reminders and alerts concerning medication refills and doctor's visits,
a conferencing subsystem the conducts conference calls among the doctor, the patient, and one or more users,
a user authentication subsystem which authenticates a family member or friend user as an authorized user before granting access to the medical information to the family member or friend user,
a level of access filter which determines one of a plurality of authorization levels, the determined level dictates to which medical information the family member or friend user is granted access, the authorization level for each authorized family member or friend user being set by the patient, the plurality of authorization levels including at least three different authorization levels.

14. The patient care network as set forth in claim 13 further including:
a data analyzer which analyzes user questions and determines whether to refer the user to a frequently asked questions database or to a medical professional.

15. The patient care network as set forth in claim 13 further including:
a presentation database that includes presentation templates and device profiles, based on a user selection and a family/friend access device profile, the central server formatting the medical information sent to each authorized user in accordance with the presentation template selected by the user and the family/friend access device profile of the family/friend device being used by the authorized user.

16. The patient care network as set forth in claim 13 further including:
an advertisement database which contains advertisements and coupons for medical services, supplies, and medications, the central server provides advertisements and coupons to one or more authorized users and the patient in accordance with at least one of a user profile, a patient profile, and the logistics support subsystem.

* * * * *